(12) United States Patent
Beck et al.

(10) Patent No.: US 8,681,007 B2
(45) Date of Patent: Mar. 25, 2014

(54) MANAGING A POTENTIAL CHOKING CONDITION WITH A MONITORING SYSTEM

(75) Inventors: Randall Beck, Cary, NC (US); Jeffrey M. Eichen, Apex, NC (US); Dale R. Hille, Raleigh, NC (US); Jan Rogoyski, Pflugerville, TX (US); Jerry A. Williams, Montezuma, IA (US)

(73) Assignee: International Business Machines Corporation, Armonk, NY (US)

( * ) Notice: Subject to any disclaimer, the term of this patent is extended or adjusted under 35 U.S.C. 154(b) by 244 days.

(21) Appl. No.: 13/344,852

(22) Filed: Jan. 6, 2012

(65) Prior Publication Data

US 2013/0176125 A1 Jul. 11, 2013

(51) Int. Cl.
*G08B 23/00* (2006.01)
(52) U.S. Cl.
USPC .................. 340/573.1; 340/572.4; 340/686.1; 340/686.6
(58) Field of Classification Search
USPC .......... 340/573.1, 572.1, 572.4, 572.8, 686.1, 340/686.6; 600/382, 529
See application file for complete search history.

(56) References Cited

U.S. PATENT DOCUMENTS

| 7,911,348 B2 | 3/2011 | Rodgers |
| 2005/0148890 A1 | 7/2005 | Hastings |
| 2009/0093687 A1* | 4/2009 | Telfort et al. ................ 600/300 |
| 2009/0209832 A1 | 8/2009 | McDaid et al. |
| 2010/0081895 A1 | 4/2010 | Zand |
| 2010/0179417 A1 | 7/2010 | Russo |
| 2011/0172561 A1* | 7/2011 | Kiani et al. .................. 600/586 |
| 2013/0090567 A1* | 4/2013 | Lee et al. ..................... 600/529 |

OTHER PUBLICATIONS

Trappey et al, "Develop Patient Monitoring and Support System Using Mobile Communication and Intelligent Reasoning", Proceedings of the 2009 IEEE International Conference on Systems, Man and Cybernetics, San Antonio, TX USA—Oct. 2009, pp. 1226-1231.
"Evaluation of the Management of Patients with Feeding and Swallowing Problems in Veterans Health Administration Facilities", Dept. of Veterans Affairs Office of Inspector General, Report No. 03-00494-110, Mar. 22, 2006.
"Aggregation of Multiple Active RFID Tags for Group-Based Events Processing", IP.com, IP.com No. IPCOM000145212D, published on the world wide web at http://ip.com/IPCOM/000145212, Jan. 10, 2007.
"Pediatric Tube Feeding", Los Altos Feeding Clinic, found on the World Wide Web at: http://www.pediatricfeeding.org/tube_feeding.html.
"Feeding Tube", Wikipedia, found on the World Wide Web at http://en.wikipedia.org/wiki/Feeding_tube#Gastric_feeding_tube.

* cited by examiner

*Primary Examiner* — Toan N Pham
(74) *Attorney, Agent, or Firm* — Paul S. Drake

(57) ABSTRACT

A method, system or computer usable program product for managing a potential choking condition with a monitoring system including monitoring by the monitoring system by detecting relative positions of a set of emitters disposed along an object, wherein a choking condition is indicated by the set of emitters being on close proximity to a neck portion of a body and arranged in a potentially choking configuration, and responsive to the determination of the choking condition, the monitoring system performing an action.

20 Claims, 6 Drawing Sheets

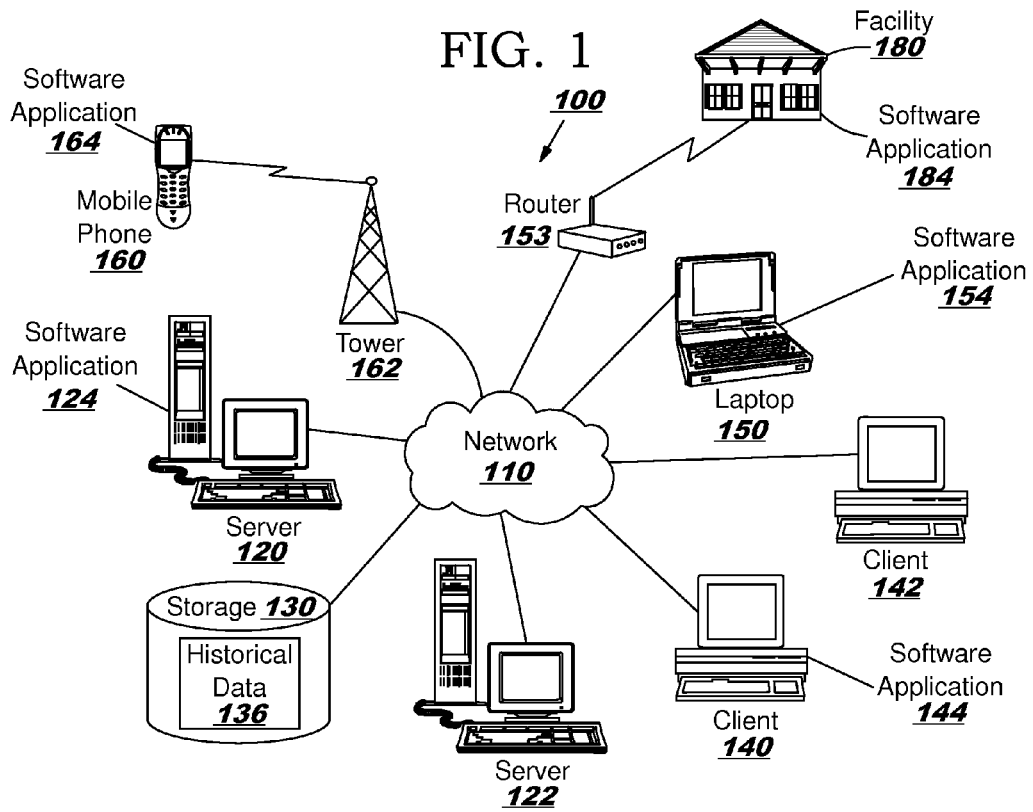
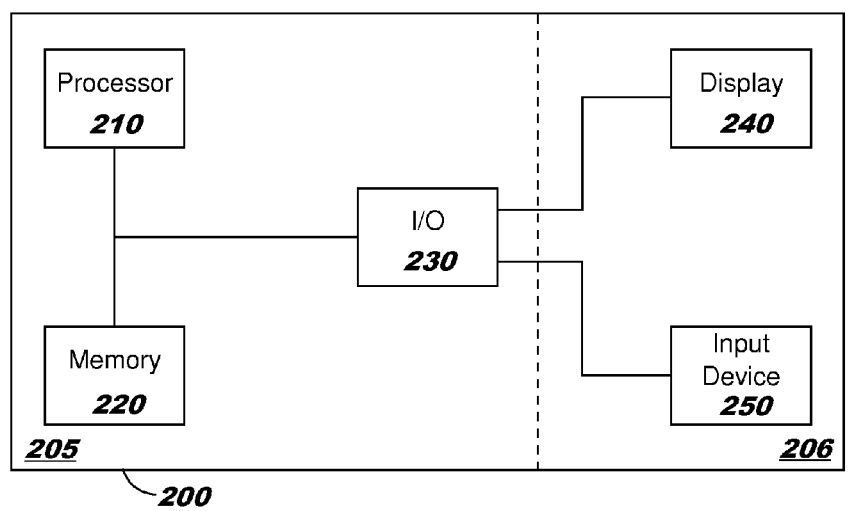

MANAGING A POTENTIAL CHOKING CONDITION WITH A MONITORING SYSTEM

BACKGROUND

1. Technical Field

The present invention relates generally to managing a potential choking condition, and in particular, to a computer implemented method for monitoring for a potential choking condition with a monitoring system which provides an alert if a potential choking condition is detected.

2. Description of Related Art

Patients may need to undergo tube feedings or intravenous tube drips over a period of hours. In such cases, where the patient has limited capacity, such as an infant or small child, such treatments may present a choking issue. That is, the patient may move around sufficiently to move the tube near and even around the patient's neck, yet not be able to remove the tube when such a condition occurs or recognize that such action is needed. The amount of tube slack remaining may be reduced to help prevent a choking condition, which results in the tube being pulled from the patient, creating a leaking and potentially a bleeding issue. In addition, without sufficient slack in the tube, a machine on the other end of the tube may be pulled and possibly fall over. However, if more slack is allowed, then a greater choking condition may occur. One attempted solution is to string the feeding or intravenous tube through a hollow flexible Styrofoam tube about three feet long, commonly referred to as a pool noodle. However, the Styrofoam tube may be used as a toy by the patient, creating additional stress and strain on the feeding tube.

In many cases, it is not practical to observe the patient during the whole period of tube feeding or intravenous tube drip. For example, for certain medical conditions, young children or infants may receive nightly tube feedings over a period of months in a home setting to maintain the child's weight and healthy growth. However, it is impractical for a parent or other caregiver to continuously observe the child patient during the many hours of the tube feeding process every night.

SUMMARY

The illustrative embodiments provide a method, system, and computer usable program product for managing a potential choking condition with a monitoring system including monitoring by the monitoring system by detecting relative positions of a set of emitters disposed along an object, wherein a choking condition is indicated by the set of emitters being on close proximity to a neck portion of a body and arranged in a potentially choking configuration, and responsive to the determination of the choking condition, the monitoring system performing an action.

BRIEF DESCRIPTION OF THE SEVERAL VIEWS OF THE DRAWINGS

The novel features believed characteristic of the invention are set forth in the appended claims. The invention itself, further objectives and advantages thereof, as well as a preferred mode of use, will best be understood by reference to the following detailed description of illustrative embodiments when read in conjunction with the accompanying drawings, wherein:

FIG. 1 is a block diagram of a network of data processing systems in which various embodiments may be implemented;

FIG. 2 is a block diagram of a data processing system in which various embodiments may be implemented;

DETAILED DESCRIPTION

Figure 3:
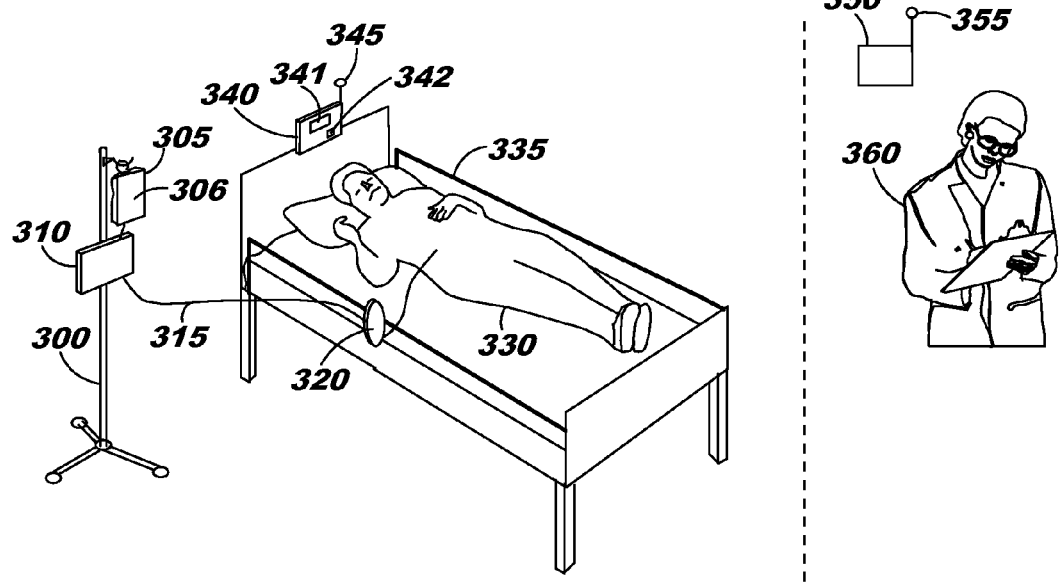
FIG. 3 is a diagram of a patient being tube fed in which various embodiments may be implemented.

Steps may be taken to monitor for a potential choking condition and providing an alert when a potential choking condition occurs. These steps may be taken as will be explained with reference to the various embodiments below.

FIG. 1 is a block diagram of a network of data processing systems in which various embodiments may be implemented. Data processing environment 100 is a network of data processing systems also known as computers or computer devices in which the embodiments may be implemented. Software applications may execute on any computer or other type of data processing system in data processing environment 100. Data processing environment 100 includes network 110. Network 110 is the medium used to provide communications links between various devices and computers connected together within data processing environment 100. Network 110 may include connections such as wire, wireless communication links, or fiber optic cables.

Servers 120 and 122 and clients 140 and 142 are coupled to network 110 along with storage unit 130. In addition, laptop 150 and facility 180 (such as a home or business) are coupled to network 110 including wirelessly such as through a network router 153. A mobile phone 160 is also coupled to network 110 through a mobile phone tower 162. Data processing systems, such as server 120 and 122, client 140 and 142, laptop 150, mobile phone 160, and facility 180 contain data and have software applications including software tools executing thereon. Other types of data processing systems such as personal digital assistants (PDAs), smartphones, tablets and netbooks may be coupled to network 110.

Server 120 may include software application 124 such as for managing a potential choking condition system for the various computer devices or other software applications in accordance with embodiments described herein. Storage 130 may contain a content source such historical data 136 for managing a potential choking condition or other content for sharing among various computer or other data processing devices. Client 140 may include software application 144. Laptop 150 and mobile phone 160 may also include software applications 154 and 164. Facility 180 may include software application 184. Other types of data processing systems coupled to network 110 may also include software applications. Software applications could include a web browser, email, or other software application that can process sensor information of a patient or other type of information to be processed.

Servers 120 and 122, storage unit 130, clients 140 and 142, laptop 150, mobile phone 160, and facility 180 and other data processing devices may couple to network 102 using wired connections, wireless communication protocols, or other suitable data connectivity. Clients 140 and 142 may be, for example, personal computers or network computers.

In the depicted example, server 120 may provide data, such as boot files, operating system images, and applications to clients 140 and 142 and laptop 150. Clients 140 and 142 and laptop 150 may be clients to server 120 in this example. Clients 140 and 142, laptop 150, mobile phone 160, and facility 180 or some combination thereof, may include their own data, boot files, operating system images, and applications. Data processing environment 100 may include additional servers, clients, and other devices that are not shown.

In the depicted example, data processing environment 100 may be the Internet. Network 110 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client server environment in which the embodiments may be implemented. A client server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications.

FIG. 2 is a block diagram of a data processing system in which various embodiments may be implemented. Data processing system 200 is an example of a computer device, such as server 120, client 140, laptop 150, mobile phone 160, or facility 180 in FIG. 1, in which computer usable program code or instructions implementing the processes may be located for the illustrative embodiments.

In the depicted example, data processing system 200 includes a CPU or central processing unit 210 which may contain one or more processors and may be implemented using one or more heterogeneous processor systems including a graphics processor. The depicted example also includes a memory 220 which may be used for storing instructions and data to be processed by CPU 210. Memory 220 may include a main memory composed of random access memory (RAM), read only memory (ROM), or other types of storage devices. Memory 210 could also include secondary storage devices such as a hard disk drive, DVD drive or other devices which may be internal or external to data processing system 200. An input output device (I/O) 230 is also shown in the depicted example for managing communications with various input devices and output devices. However, other examples could use the CPU to communicate directly with various input or output devices or use separate input and output controllers.

In the depicted example, a computer display 240 is shown for the data processing system to communicate with a user or another data processing system. Other types of output devices may be used such as an audio device. An input device 250 is also shown which may be a keyboard, mouse, a touch sensitive display, or other types of input devices.

Data processing system 200 is shown with an internal section 205 and an external section 206. Often input and output devices may be physically separate from but connected to the CPU and memory. However, that is often not the case with portable devices such as mobile phones.

An operating system may run on processor 210. The operating system coordinates and provides control of various components within data processing system 200 in FIG. 2. The operating system may be a commercially available operating system. An object oriented programming system may run in conjunction with the operating system and provides calls to the operating system from programs or applications executing on data processing system 200. Instructions for the operating system, the object-oriented programming system, and applications or programs may be located on secondary storage devices such a hard drive, and may be loaded into RAM for execution by processing unit 210.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1 and 2. In addition, the processes of the embodiments may be applied to a multiprocessor data processing system.

The depicted examples in FIGS. 1-2 and above described examples are not meant to imply architectural limitations. For example, data processing system 200 may also be a mobile phone 160, tablet computer, laptop computer, or telephone device.

FIG. 3 is a diagram of a patient being tube fed in which various embodiments may be implemented. A patient may be a person or animal in a medical, home or any other setting including any non-medical setting. An IV (intravenous) pole 300 is shown holding a bag 305 containing fluids 306 and an optional pump 310. A tube 315 runs from the bag through the pump through a tensioner 320 to a patient 330. In this case, the tube is shown as a feeding tube which is connected to a gastric feeding tube (G-tube) located on the patient's abdomen. Alternatively the tube may be connect to the patient in a variety of locations such as the hand or wrist where a PICC (peripherally inserted central catheter) line may be located for providing intravenous solutions such as plasma, or through the nose to the patient's stomach for feeding solutions. Tube 315 includes a set of emitters (at least one) that are detectable. This set of emitters may be passive or active. Examples of passive emitters include RFIDs, luminescence, colored tags, or other devices that may be powered by an external source. Examples of active emitters include certain RFID tags or other active devices. Patient 330 may be located in a crib 335, or alternatively a bed or other rest area depending on the age or capacity/incapacity of the patient.

Located near the patient is a monitoring system 340 with an input/output device 341, software 342 and antenna 345. Monitoring system input/output device 341 may be a touch sensitive display, a combination of buttons and display, or other forms of input and output devices. Input/output device 341 may also include an RFID (radio frequency identification) device, a video camera, or other devices for sensing the position of the tube (including the set of emitters) and the patient. Software 342 is used to manage the operations of the monitoring system including communications with other devices.

Monitoring system 340 may be a specially designed device for use in this type of setting, or it may be a common device such as a desktop computer, a server, a laptop or even a mobile phone. In the example of a mobile phone, software 342 may be an application on the mobile phone, an RFID sensor may be coupled to the mobile phone such as through a Wi-Fi, Bluetooth or other wireless or wired connection for providing sensory data about the tube and patient.

An alert system 350 with an antenna 355 may be located near a caretaker 360 of the patient. The caretaker may be a nurse in a hospital setting, a parent in a home setting, or other type of caretaker. The monitoring system and alert system communicate with each other through their antennas, but such communication may also occur with wires such as in a hospital setting. If the monitoring system is a mobile phone, the alert system may also be a mobile phone which may be automatically contacted by the monitoring system mobile phone in case of an alert condition. In an alternative embodiment, monitoring system 340 may contain the alert system such as where the monitoring system may generate an alert by simply sounding an audible alarm.

Monitoring system 340 may be in communication with tensioner 320 where the tensioner may be instructed to loosen, tighten or even sever the tube depending on monitored conditions of the tube and patient. The communications may be wired or wireless, such as through an antenna or through other means such as photonically or even aurally. The monitoring system and tensioner may also be combined as a single unit.

Monitoring system 340 may be in communication with pump 310. The communications may be wired or wireless, such as through an antenna or through other means such as photonically or even aurally. In case the monitoring system determines that the tube needs to be severed by tensioner 320 or that the tube is no longer properly providing the fluids to the patient, then the pump may be instructed to stop pumping fluids.

Monitoring system 340 may also communicate with various data processing systems such as a remote server through the internet. These communications could be used for periodically downloading historical data which may be reviewed for trends and communicated to a physician. Historical data may also be used to modify the sensitivity of the monitoring system over time.

Monitoring system 340 may have a reset button for a caretaker to press after an alert has been generated. The monitoring system may also have a false alarm button which acts as a reset button, but also indicates to the monitoring system that changes can be made to the sensitivity of the monitoring system to help prevent future false alarms. Monitoring system 340 may also have a learning mode. In this mode the feeding tube may be positioned in several locations relative to the patient followed by an indication whether the position is a potentially choking configuration indicating a choking condition or not. These potentially choking configurations may be stored in memory of the monitoring system and matched against sensed configurations later for determining whether a choking condition has occurred.

Figure 4A:
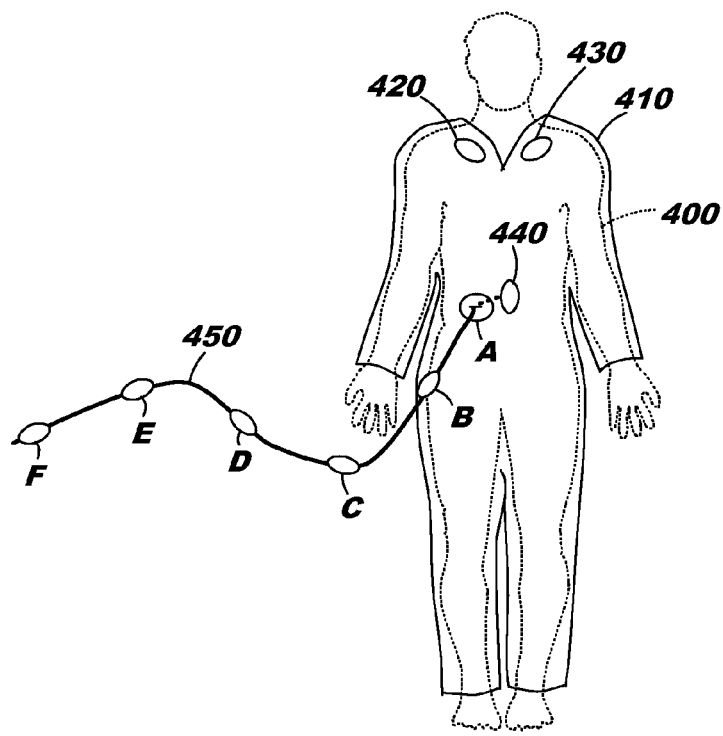
FIG. 4A is a diagram of a patient being fed through a feeding tube in accordance with a first embodiment of the invention.

FIG. 4A is a diagram of a patient 400 being fed through a feeding tube in accordance with a first embodiment of the invention. In the example provided, the patient shown is an infant human although this embodiment may be implemented with older humans or even various animals including dogs or cats. A patient may be a person or animal in a medical, home or any other setting including any non-medical setting. The patient is wearing a one piece outfit 410 with three RFIDs (radio frequency identifiers) 420, 430 and 440 located at specific locations in the one piece outfit. RFIDs 420 and 430 are located at the neck area of the body of the patient when the one piece outfit is worn. RFID 440 is located near the G-tube of the patient. These RFIDs may be sewn into or clipped to the outfit. Other methods may be used to attach the RFIDs to desired locations on the outfit including taping directly to the skin of the patient or using various strapping mechanisms.

Also shown is a feeding tube 450 tethered to the patient with a series of RFIDs A, B, C, D, E and F located on the feeding tube. The monitoring system is able to locate the various RFIDs and their relative positions to determine if any dangerous conditions occur. The location and relative position of these RFIDs may be detected by an RFID detector embedded in or coupled to the monitoring system. In this example, RFID A at the end of the feeding tube is located very closely to RFID 440 which is at the G-tube location and near a small hole in the outfit allowing the feeding tube to travel through the outfit to the G-tube location. So long as the feeding tube is properly inserted, this condition should continue. Also, none of the other RFIDs B through F is near the neck area RFIDs 420 and 430, as a result the RFIDs are not in a potentially choking configuration so no choking hazard is detected.

FIGS. 4B through 4E are diagrams of the relative positions of RFIDS (radio frequency identifiers) in various scenarios in accordance to a first embodiment. These figures show a subset of the items shown in FIG. 4A for ease of reference. Only the top portion of one piece outfit 410 is shown with the RFIDs embedded in the outfit. Also shown is the feeding tube 450 with multiple RFIDs embedded in that tube.

Figure 4B:
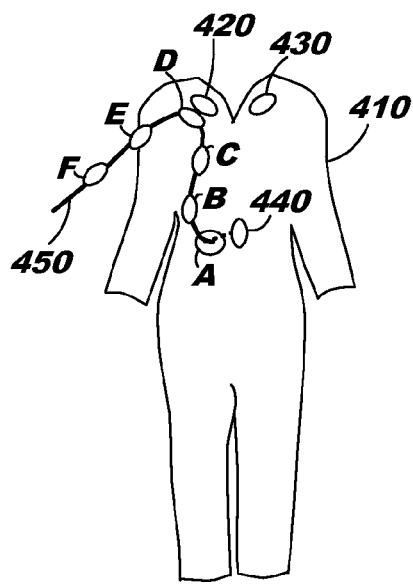
FIGS. 4B through 4E are diagrams of the relative positions of RFIDS (radio frequency identifiers) in various scenarios in accordance to a first embodiment.
Figure 4C:
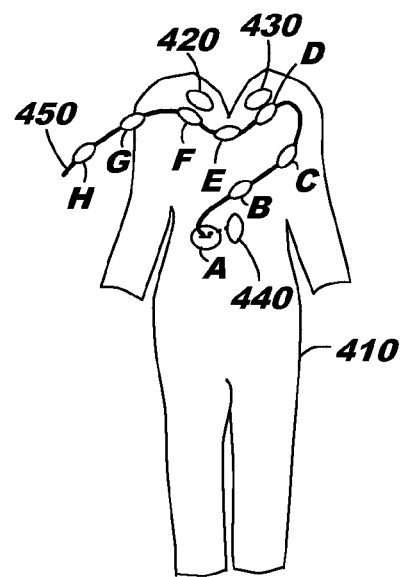
Figure 4D:
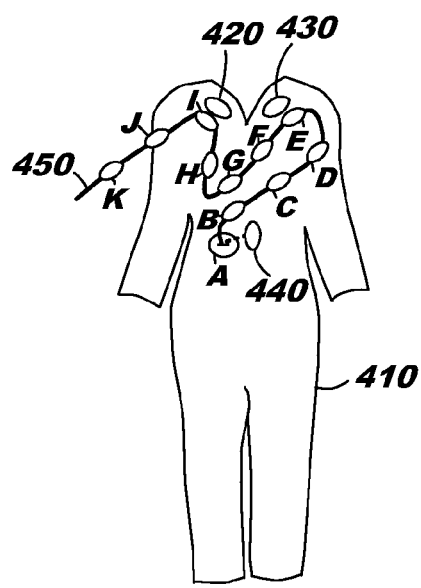
Figure 4E:
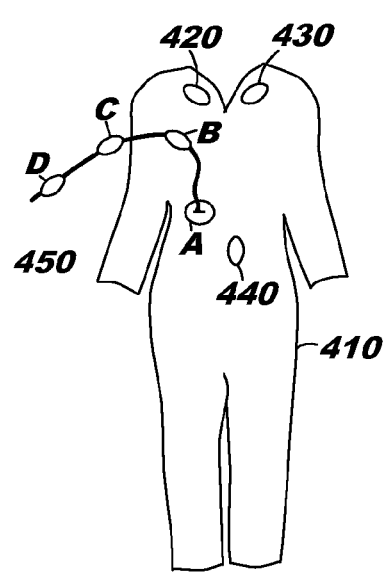

In FIG. 4B, feeding tube RFID D is located close to neck area RFID 420. However, there is no feeding tube RFID close to RFID 430, as a result there is no potentially choking configuration so no choking threat is imminent. In FIG. 4C, feeding tube RFID D is close to RFID 430 and feeding tube RFID F is close to RFID 420. As a result, there is a potentially choking configuration, a choking condition may occur, so an alert is generated. In addition, the tensioner may be instructed to either loosen or sever the feeding tube. If severed, the pump would also be instructed to cease pumping fluids. In FIG. 4D, feeding tube RFID E is close to RFID 430 and feeding tube RFID I is close to RFID 420. Since feeding tube RFIDs E and I are so far apart, there is a lot of slack in the line, so there is no potentially choking condition, a choking condition is not imminent and no alarm is generated. The tensioner may be instructed to tighten the line somewhat to see if that pulls feeding tube RFID I away from the patients neck. If not, then the tensioner would be instructed to loosen the line and an alert may be generated. In FIG. 4E, feeding tube RFID A is not located close to RFID 440, indicated the feeding tube may not be connected to the G-tube. As a result, feeding solution may be leaking onto the bed and the patient will not be fed. The pump may be instructed to stop pumping to prevent leakage and an alert is generated to instruct the caretaker to reinsert the feeding tube.

Although the patient is shown lying on the back, RFIDs allow this embodiment to work when the patient is in any position. The locations of the RFIDs may be determined in three dimensions, allowing various techniques to detect choking or other conditions requiring attention by a caretaker.

Figure 5A:
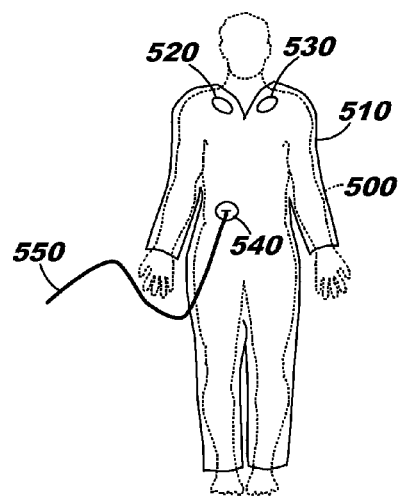
FIG. 5A is a diagram of a patient being fed through a feeding tube in accordance with a second embodiment of the invention.

FIG. 5A is a diagram of a patient 500 being fed through a feeding tube in accordance with a second embodiment of the invention. In the example provided, the patient shown is an infant human although this embodiment may be implemented with older humans or even various animals including dogs or cats. A patient may be a person or animal in a medical, home or any other setting including any non-medical setting. The patient is wearing a one piece outfit 510 with three luminescent areas 520, 530 and 540 located at specific locations in the one piece outfit. Luminescent areas 520 and 530 are located at the neck area of the body of the patient when the one piece outfit is worn. Luminescent area 540 is located near the G-tube of the patient at a hole in the outfit where the feeding tube may travel through the outfit to the G-tube. These luminescent areas may be luminescent patches sewn into or clipped to the outfit including using Velcro. Other methods may be used to attach the luminescent areas to desired locations on the outfit including taping directly to the skin of the patient or using various strapping mechanisms. The luminescence is preferably photoluminescence which may be enhanced by the use of a low dose black light or other similar light source. Other types of luminescent materials may be used.

Also shown is a luminescent feeding tube 550 tethered to the patient. The feeding tube is preferably a different luminescent color than the luminescent areas on the patients outfit. The monitoring system is able to locate the various luminescent areas and their relative positions to determine if any dangerous conditions occur. The location and relative position of these luminescent areas may be detected by a photosensitive detector such as a video camera embedded in or coupled to the monitoring system. In this example, an end portion of the feeding tube is located very closely to luminescent area 540 which is near the G-tube location. So long as the feeding tube is properly inserted, this condition should continue. Also, none of the luminescent feeding tube is near the luminescent areas 520 and 530, so there is no potentially choking configuration and no choking hazard is detected.

FIGS. 5B through 5E are diagrams of the relative positions of the luminescent tube to the luminescent areas in various scenarios in accordance to a second embodiment. These figures show a subset of the items shown in FIG. 5A for ease of reference. Only the top portion of one piece outfit 510 is shown with the luminescent areas embedded in the outfit. Also shown is the luminescent feeding tube 450.

Figure 5B:
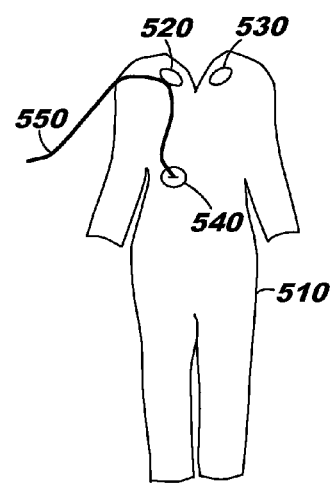
FIGS. 5B through 5E are diagrams of the relative positions of the luminescent tube to the luminescent areas in various scenarios in accordance to a second embodiment.
Figure 5C:
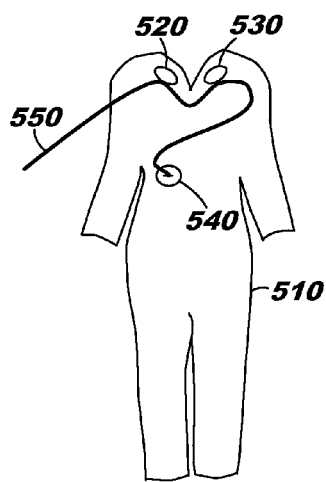
Figure 5D:
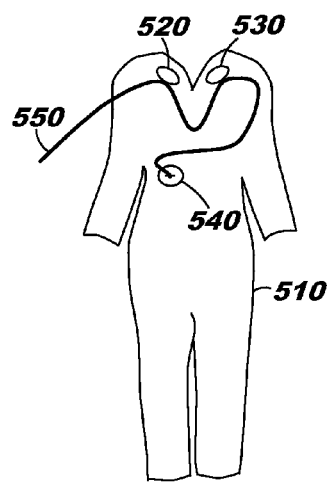
Figure 5E:
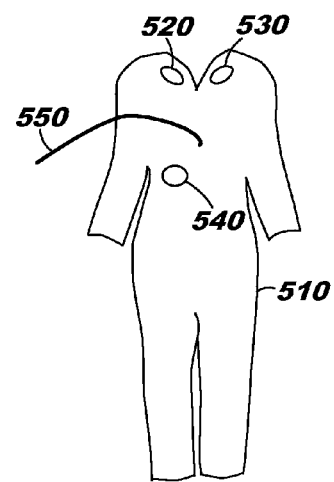

In FIG. 5B, part of the feeding tube is located close to neck area 520. However, the feeding tube is not close to neck area 530, there is no potentially choking condition so no choking threat is imminent. In FIG. 5C, one part of the feeding tube is close to neck area 530 and another portion of the feeding tube is close to neck area 520. As a result, a choking condition may occur, so an alert is generated. In addition, the tensioner may be instructed to either loosen or sever the feeding tube. If severed, the pump would also be instructed to cease pumping fluids. In FIG. 5D, a portion of the feeding tube is close to neck area 430 and another portion of the feeding tube is close to neck area 420. However, there is a significant length of the feeding tube between the neck areas which can be detected, resulting in a lot of slack in the line, so a choking condition is not imminent and no alarm is generated. The tensioner may be instructed to tighten the line somewhat to see if that pulls part of the feeding tube away from the patients neck. If not, then the tensioner would be instructed to loosen the line and an alert may be generated. In FIG. 5E, the feeding tube is not located close to luminescent area 540, indicating the feeding tube may not be connected to the G-tube. As a result, feeding solution may be leaking onto the bed and the patient will not be fed. The pump may be instructed to stop pumping to prevent leakage and an alert is generated to instruct the caretaker to reinsert the feeding tube.

Other similar techniques could be used in alternative embodiments. For example, if the fluid has a temperature different from the patient's body, infrared sensors could identify the location of the feeding tube. Also, various types of photoelectric sensors may also be used to locate the tube depending on conditions and the type of tube being used. As another example, the patients outfit may be one color, the neck and G-tube areas another color, and the feeding tube a third color, all detectable by various types of sensors.

Figure 6:
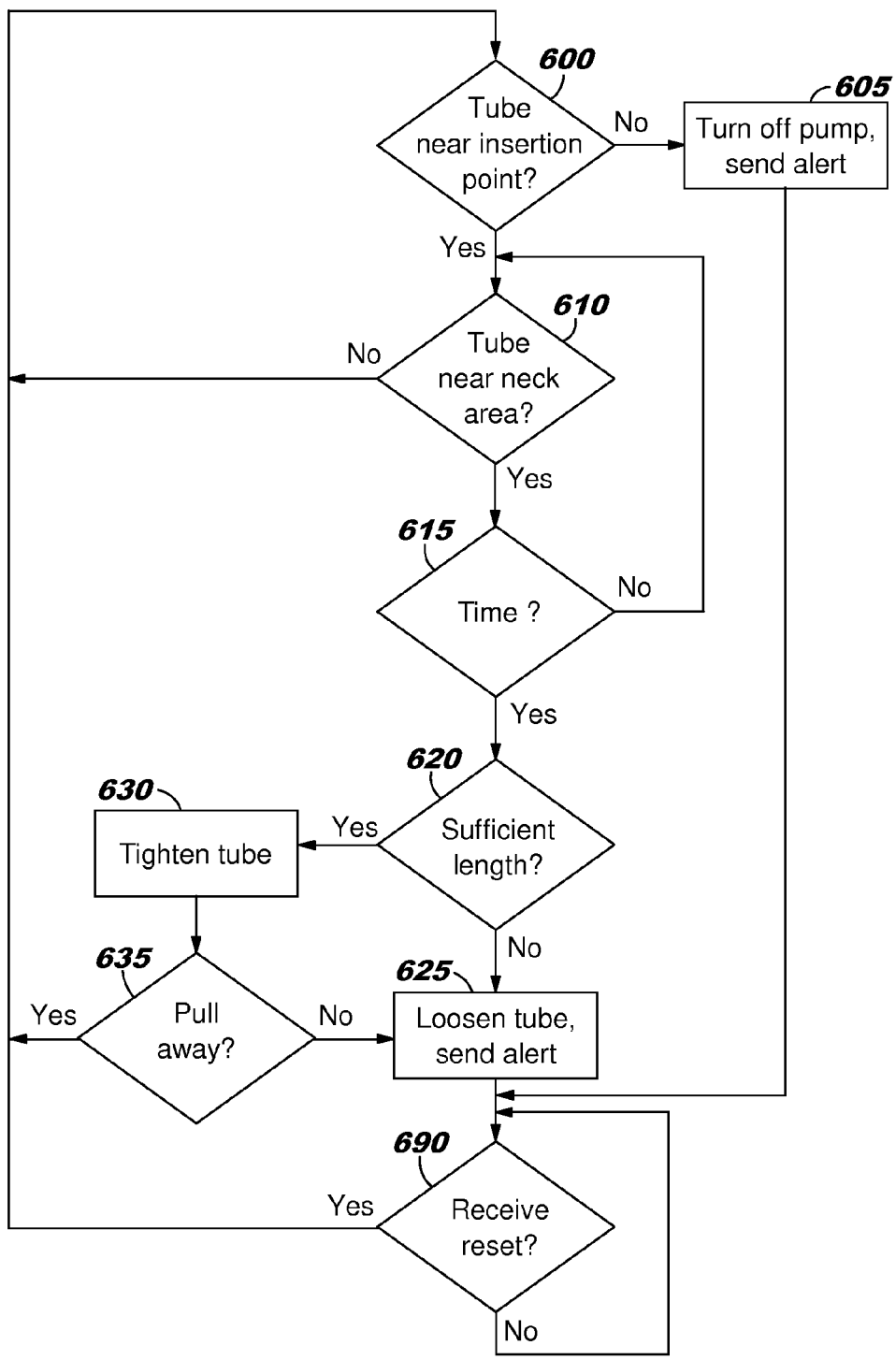
FIG. 6 is a flowchart of the operation of the monitoring system utilizing the first or second embodiments.

FIG. 6 is a flowchart of the operation of the monitoring system utilizing the first or second embodiments.

In a first step 600, the monitoring system determines whether an end of the feeding tube is located near the insertion point of the patient. In the case of a feeding tube, this would be near the G-tube. In the case of an intravenous tube, this may be near the PICC line. For the first embodiment, this is accomplished by determining the distance between the feeding tube A RFID and RFID 440. For the second embodiment, this is accomplished by determining the distance between the detected end of the feeding tube and the luminescent area 540. If not, then processing continues to step 605 where the monitoring system enters a state where the pump is turned off and an alert is sent to the caretaker. Processing would then continue to step 690 where the monitoring system enters a state where processing stops until the monitoring system is reset by the caretaker such as by pressing a reset button on the monitoring system. A false alarm button may also be pressed which also resets the monitoring system, but also indicates that the sensitivity of the monitoring system may be reduced to reduce the number of future false alarms.

If yes in step 600, then processing continues to step 610 where the monitoring system determines whether the feeding tube is near both neck areas of the body of the patient. In the first embodiment, this is accomplished by determining whether any two of the RFIDs are located close to the neck area RFID 420 and neck area RFID 430. In the second embodiment, this is accomplished by determining whether one part of the feeding tube is close to neck area 520 and another portion of the feeding tube is close to neck area 530. If not, then processing returns to step 600 to restart the monitoring process. If yes, then processing continues to step 615.

In step 615 it is determined whether the tube has been close to the neck of the patient for a sufficient period of time. This allows the system to discount a temporary condition that may occur as the patient is moving. The amount of time is preferably predetermined by a medical professional and may be more than a few seconds, but probably not longer than a minute or so in case a potential choking condition has occurred. If not a sufficient period of time, processing returns to step 610. Otherwise processing continues to step 620.

In step 620, the monitoring system enters a state where the monitoring system determines whether there is a sufficient length of tube between the parts of the tube close to the patient's neck area. In the first embodiment, this would be by determining the number of RFIDs (indicating the length of tube) between the RFIDs close to the neck area. In the second embodiment, this would be determined visually detection of the tube. If no, the processing continues to step 625 where the tensioner is instructed by the monitoring system to loosen the tube and an alert is sent to the caretaker. Processing would then continue to step 690 where the monitoring system enters a state where processing would pause until the monitoring system is reset.

If yes in step 620, then processing continues to step 630 where the tensioner is instructed to slightly tighten the tube. Processing then continues to step 635 where it is determined whether tightening the tube pulled the tube away from at least one side of the neck. In the first embodiment, this is accomplished by determining whether either or both tube RFID close to the neck area RFIDs is pulled away. In the second embodiment, this is accomplished by visually observing whether the part of the tube closest to either neck area is pulled away. If yes, then processing returns to step 600 to restart the monitoring process. If not, then processing continues to step 625 where the tensioner is instructed to loosen the tube and an alert is sent to the caretaker.

In step 690, an alternative embodiment may generate an alert to a remote emergency worker if the reset is not received within a period of time. For example, if the caretaker is unable to respond, then an emergency worker may be contacted in order to handle the choking condition.

Additional sensors may be utilized to help diagnose a potential choking configuration indicating a choking condition. For example, a blood oxygen sensor on the patient may provide additional information about the condition of the patient to help prevent false positives.

The monitoring system may also download historical data, such as the time and nature of alerts generated, to a central database periodically or on demand. This would allow a medical professional to review the data and make appropriate adjustments. For example, the period of time in step 615 above may be lengthened or shortened. In addition, additional sensors or alternative therapies may be recommended for the patient.

Figure 7:
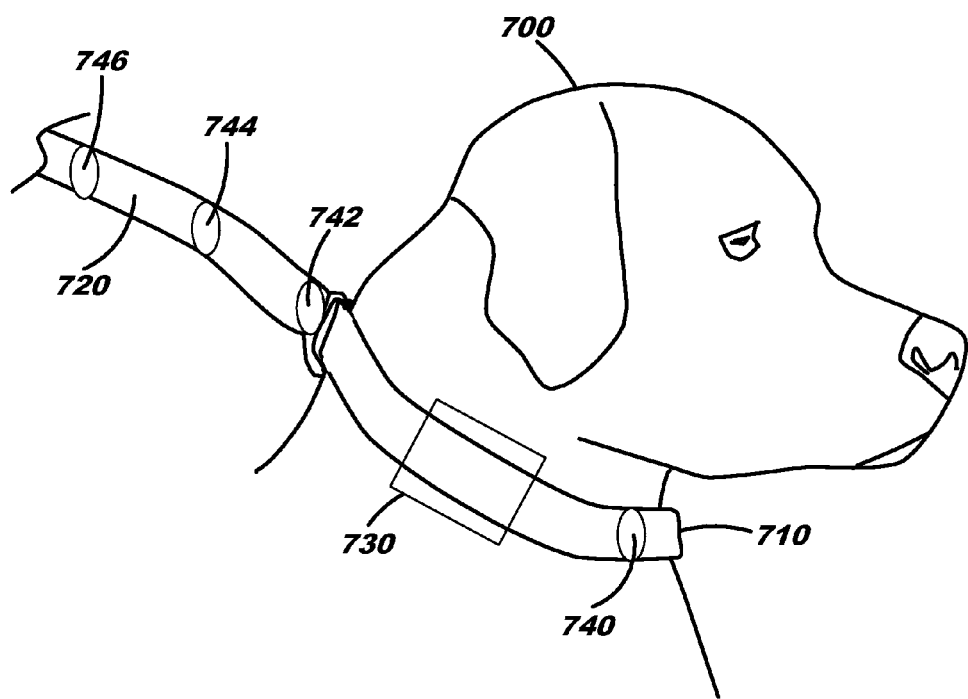
FIG. 7 is a diagram of a dog on a leash in accordance with a third embodiment of the invention.

FIG. 7 is a diagram of a dog 700 on a leash in accordance with a third embodiment of the invention. Dogs can put themselves in potentially choking configuration resulting in a choking condition when leashed to a pole or other object. Dogs tend to move around and often end up wrapping the leash around the pole until a choking condition occurs. Although a dog is shown, the embodiment could be implemented with a variety of other types of animals such as cats or any other type of patient. A patient may be a person or animal in a medical, home or any other setting including any non-medical setting.

Dog 700 wears a collar 710 around the neck area of the body of the dog and is tethered on a leash 720. The collar also has a RFID detector and monitoring system 730. Multiple RFIDs 740, 742, 744 and 746 are located on the collar and leash. If the dog has wrapped the leash around an object then one of the RFIDs on the leash may be close to the RFID detector. If the dog has caught the leash on an object above the dog, then the leash may be stretched excessively and the RFIDs on the collar may be further away than desirable again choking the dog.

In either condition, the RFID detector can detect such potential choking conditions and alert the dog owner. The process for detecting such conditions and alerting the owner can be very similar to the processes described with reference to FIG. 5A above.

There are other types of choking conditions that may be detected and prevented by alerting caretakers for people and pets in a variety of situations. One of ordinary skill in the art can adopt the present invention for those conditions.

The invention can take the form of an entirely software embodiment, or an embodiment containing both hardware and software elements. In a preferred embodiment, the invention is implemented in software or program code, which includes but is not limited to firmware, resident software, and microcode.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM), or Flash memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Further, a computer storage medium may contain or store a computer-readable program code such that when the computer-readable program code is executed on a computer, the execution of this computer-readable program code causes the computer to transmit another computer-readable program code over a communications link. This communications link may use a medium that is, for example without limitation, physical or wireless.

A data processing system suitable for storing and/or executing program code will include at least one processor coupled directly or indirectly to memory elements through a system bus. The memory elements can include local memory employed during actual execution of the program code, bulk storage media, and cache memories, which provide temporary storage of at least some program code in order to reduce the number of times code must be retrieved from bulk storage media during execution.

A data processing system may act as a server data processing system or a client data processing system. Server and client data processing systems may include data storage media that are computer usable, such as being computer readable. A data storage medium associated with a server data processing system may contain computer usable code such as code for evaluating sensor data for managing a potential choking condition. A client data processing system may download that computer usable code, such as for storing on a data storage medium associated with the client data processing system, or for using in the client data processing system. The server data processing system may similarly upload computer usable code from the client data processing system such as a content source. The computer usable code resulting from a computer usable program product embodiment of the illustrative embodiments may be uploaded or downloaded using server and client data processing systems in this manner.

Input/output or I/O devices (including but, not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to explain the principles of the invention, the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for managing a potential choking condition with a monitoring system comprising:
    monitoring by the monitoring system by detecting relative positions of a set of emitters disposed along an object, wherein a choking condition is indicated by the set of emitters being on close proximity to a neck portion of a body and arranged in a potentially choking configuration; and
    responsive to the indicated choking condition, the monitoring system performing an action.

2. The method of claim 1 wherein the action is based on a state of the monitoring system.

3. The method of claim 1 wherein the set of emitters comprises a first RFID tag and a second RFID tag; wherein the object comprises a tether with a plurality of RFID tags along the tether; and wherein the monitoring system comprises a RFID reader and a remote monitoring station.

4. The method of claim 3 wherein detecting a first tether RFID of the plurality of RFID tags in close proximity to the first RFID tag and detecting a second tether RFID of the plurality of RFID tags in close proximity to the second RFID tag generates the determination of the choking condition.

5. The method of claim 4 wherein the choking condition is characterized based on a distance along the tether between the first tether RFID tag and the second tether RFID tag.

6. The method of claim 3 wherein the tether further comprises a tensioner on the tether, and the action is selected from a list consisting of releasing the tensioner, tightening the tensioner, sounding an audible alarm, and not sounding the audible alarm.

7. The method of claim 1 wherein the set of emitters comprises a first RFID tag and a second RFID tag;
    wherein the object comprises a tether with a plurality of RFID tags along the tether and wherein the tether further comprises a tensioner on the tether;
    wherein the monitoring system comprises a RFID reader and a remote monitoring station;
    wherein detecting a first tether RFID of the plurality of RFID tags in close proximity to the first RFID tag and detecting a second tether RFID of the plurality of RFID tags in close proximity to the second RFID tag generates the indicated choking condition;
    wherein the choking condition is characterized based on a distance along the tether between the first tether RFID tag and the second tether RFID tag; and
    wherein the action is based on a state of the monitoring system and the action is selected from a list consisting of releasing the tensioner, tightening the tensioner, sounding an audible alarm, and not sounding the audible alarm.

8. The method of claim 1 wherein the set of emitters comprises a first luminescent area and a second luminescent area; wherein the object comprises a luminescent tether; and wherein the monitoring system comprises a photosensitive detector and a remote monitoring station.

9. The method of claim 8 wherein detecting the luminescent tether in close proximity to the first luminescent area and detecting the luminescent tether in close proximity to the second luminescent area generates the indicated choking condition.

10. The method of claim 1 wherein the set of emitters comprises at least one RFID reader positioned around the neck portion of the body; wherein the object comprises a tether with a plurality of RFID tags along the tether; and
    wherein the monitoring system comprises a RFID reader and a remote monitoring station.

11. The method of claim 10 wherein detecting at least one of the plurality of RFIDS in an undesirable location generates the indicated choking condition.

12. A computer usable program product comprising a computer usable storage medium including computer usable code for managing a potential choking condition by a monitoring system, the computer usable program product comprising code for performing the steps of:

monitoring by the monitoring system by detecting relative positions of a set of emitters disposed along an object, wherein a choking condition is indicated by the set of emitters being on close proximity to a neck portion of a body and arranged in a potentially choking configuration; and responsive to the indicated choking condition, the monitoring system performing an action.

13. The computer usable program product of claim 12 wherein the set of emitters comprises a first RFID tag and a second RFID tag; wherein the object comprises a tether with a plurality of RFID tags along the tether; and wherein the monitoring system comprises a RFID reader and a remote monitoring station.

14. The computer usable program product of claim 13 wherein detecting a first tether RFID of the plurality of RFID tags in close proximity to the first RFID tag and detecting a second tether RFID of the plurality of RFID tags in close proximity to the second RFID tag generates the indicated choking condition.

15. The computer usable program product of claim 14 wherein the choking condition is characterized based on a distance along the tether between the first tether RFID tag and the second tether RFID tag.

16. A data processing system for managing a potential choking condition, the data processing system comprising:

a processor; and a memory storing program instructions which when executed by the processor execute the steps of:

monitoring by the monitoring system by detecting relative positions of a set of emitters disposed along an object, wherein a choking condition is indicated by the set of emitters being on close proximity to a neck portion of a body and arranged in a potentially choking configuration; and responsive to the indicated choking condition, performing an action.

17. The data processing system of claim 16 wherein the set of emitters comprises a first RFID tag and a second RFID tag; wherein the object comprises a tether with a plurality of RFID tags along the tether; and further comprising a monitoring system comprises a RFID reader and a remote monitoring station.

18. The data processing system of claim 17 wherein detecting a first tether RFID of the plurality of RFID tags in close proximity to the first RFID tag and detecting a second tether RFID of the plurality of RFID tags in close proximity to the second RFID tag generates the indicated choking condition.

19. The data processing system of claim 18 wherein the choking condition is characterized based on a distance along the tether between the first tether RFID tag and the second tether RFID tag.

20. The data processing system of claim 17 wherein the tether further comprises a tensioner on the tether, and the action is selected from a list consisting of releasing the tensioner, tightening the tensioner, sounding an audible alarm, and not sounding the audible alarm.

* * * * *